United States Patent [19]

Lee et al.

[11] Patent Number: 4,733,610

[45] Date of Patent: Mar. 29, 1988

[54] 3-NITRO-1,2,4-TRIAZOL-5-ONE, A LESS SENSITIVE EXPLOSIVE

[75] Inventors: Kien-Yin Lee; Michael D. Coburn, both of Los Alamos, N. Mex.

[73] Assignee: The United States of America as represented by the United States Department of Energy, Washington, D.C.

[21] Appl. No.: 9,165

[22] Filed: Jan. 30, 1987

[51] Int. Cl.$^4$ ............................................. F42B 3/00
[52] U.S. Cl. .................................... 102/332; 102/301; 102/306; 149/88; 149/109.4; 149/109.6; 548/263; 548/265; 548/266
[58] Field of Search .................... 149/88, 109.4, 109.6; 548/263, 265, 266; 106/306, 332, 301

[56] References Cited

U.S. PATENT DOCUMENTS

| | | | |
|---|---|---|---|
| 3,043,848 | 7/1962 | Hageman | 149/88 |
| 3,054,800 | 9/1962 | Burchfield et al. | 149/88 |
| 3,111,524 | 11/1963 | Wiley et al. | 149/88 |
| 3,165,753 | 1/1965 | Smith et al. | 149/88 |

OTHER PUBLICATIONS

G. I. Chipen, R. P. Bokalder, and V. Ya. Grinshtein, "1,2,4,-Triazol-3-One and its Nitro and Amino Derivatives," Khim. Getero. Soed. 2, 110 (1966).

T. P. Kofman, M. S. Pevzner, L. N. Zhukova, T. A. Kravchenko, and G. M. Frolova, "Methylation of 3-Nitro-1,2,4-Triazol-5-One," Zhurnal Organicheskol Khimii 16, 420 (1980).

Kien-Yin Lee and Michael D. Coburn, "3-Nitro-1,2,4-Triazol-5-One, A Less Sensitive Explosive," Los Alamos National Laboratory Report LA-10302-MS, made available to the public on or about the 21st week of 1986 through the National Technical Information Service (Stock No. DE 86009789).

*Primary Examiner*—Stephen J. Lechert, Jr.
*Attorney, Agent, or Firm*—Samuel M. Freund; Paul D. Gaetjens; Judson R. Hightower

[57] ABSTRACT

A less sensitive explosive, 3-nitro-1,2,4-triazol-5-one. The compound 3-nitro-1,2,4-triazol-5-one (NTO) has a crystal density of 1.93 g/cm$^3$ and calculated detonation velocity and pressure equivalent to those of RDX. It can be prepared in high yield from inexpensive starting materials in a safe synthesis. Results from initial small-scale sensitivity tests indicate that NTO is less sensitive than RDX and HMX in all respects. A 4.13 cm diameter, unconfined plate-dent test at 92% of crystal density gave the detonation pressure predicted for NTO by the BKW calculation.

6 Claims, No Drawings

3-NITRO-1,2,4-TRIAZOL-5-ONE, A LESS SENSITIVE EXPLOSIVE

This invention is the result of a contract with the Department of Energy (Contract No. W-7405-ENG-36).

BACKGROUND OF THE INVENTION

The present invention relates generally to methods of providing explosive chemical energy to objects and, more particularly, to methods for providing shock and impact insensitive explosive chemical energy to objects.

In the past, the more common explosives, such as RDX, HMX, and TNT, were considered adequate for all weapons applications. However, as a result of many explosions resulting from the unintentional initiation of munitions by either impact or shock aboard cargo ships, aircraft carriers, and ammunition trains, these explosives have become less attractive. Triaminotrinitrobenzene (TATB) is currently employed for insensitive high explosive applications in nuclear weapons, but this explosive does not provide sufficiently high energetic performance in order for it to replace RDX and HMX in some applications. Therefore, there is a continuing need for explosives which are powerful, yet resistant to accidental and sympathetic initiation.

A journal article entitled, "1,2,4,-Triazol-3-One and its Nitro and Amino Derivatives," by G. I. Chipen, R. P. Bokalder, and V. Ya. Grinshtein, Khim, Getero. Soed. 2, 110 (1966), describes the preparation of 3-nitro-1,2,4-triazol-5-one, but does not suggest or teach the use of this material as an explosive.

In "Methylation of 3-Nitro-1,2,4-Triazol-5-One," by T. P. Kofman, M. S. Pevzner, L. N. Zhukova, T. A. Kravchenko, and G. M. Frolova, Zhurnal Organicheskoi Khimii 16, 420 (1980), the authors teach the methylation of 3-nitro-1,2,4-triazol-5-one. Again, the authors thereof do not suggest nor teach the use of this material for other than a starting material in chemical syntheses.

Accordingly, it is an object of the present invention to provide a method for applying impact and shock insensitive explosive chemical energy to objects.

Another object of our invention is to provide a method for applying high detonation pressure, impact, and shock insensitive explosive chemical energy to objects.

Yet another object of the present invention is to provide a method for applying high detonation pressure, impact, and shock insensitive explosive chemical energy to objects using materials which can be prepared from inexpensive starting materials.

Still another object of the present invention is to provide a method for applying shock and impact insensitive, high detonation pressure explosive chemical energy to objects using materials which can be pressed without the use of binder materials into desired shapes having high density.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method hereof includes the step of detonating a composition of matter which includes 3-nitro-1,2,4-triazol-5-one (NTO).

In a further aspect of the present invention, in accordance with its objects and purposes, the method hereof includes the step of detonating a composition of matter which consists essentially of 3-nitro-1,2,4-triazol-5-one (NTO).

In yet a further aspect of the present invention, in accordance with its objects and purposes, the method hereof includes the steps of pressing a composition of matter consisting essentially of 3-nitro-1,2,4-triazol-5-one (NTO) into a desired shape, and detonating the shape so produced.

Benefits and advantages of the subject method include decreased sensitivity of the material utilized to detonation by shock and impact from that of RDX and TNT, while providing a high detonation pressure. Moreover, NTO can easily be pressed without a binder into desired shapes having high density, and be prepared from low cost starting materials.

DETAILED DESCRIPTION OF THE INVENTION

Reference will now be made in detail to the present preferred embodiment of the invention. Briefy, our invention includes the use of 3-nitro-1,2,4-triazol-5-one as an explosive having high detonation pressure and low sensitivity to detonation by shock and impact.

NTO is prepared by a modification of the procedure reported in the Chipen et al. article mentioned hereinabove. The intermediate, 1,2,4-triazol-5-one (TO), is first prepared and then nitrated with 70% nitric acid.

I. Preparation of TO (2 mol):

NTO is prepared by condensing semicarbazide hydrochloride and formic acid, according to Equation 1 hereinbelow. Hydrochloric acid is released. Accordingly, 230 ml of formic acid (85%) was added to 223 g of semicarbazide hydrochloride in a 1 l, 3-necked round bottom flask, and the mixture is heated with stirring until all of the semicarbazide hydrochloride is dissolved. To remove excess formic acid, the mixture was concentrated by distillation until crystallization occurred. Water (approximately 300 ml) is added and distillation is continued until the mixture is near dryness. The mixture is cooled to below 30° C. in preparation for nitration.

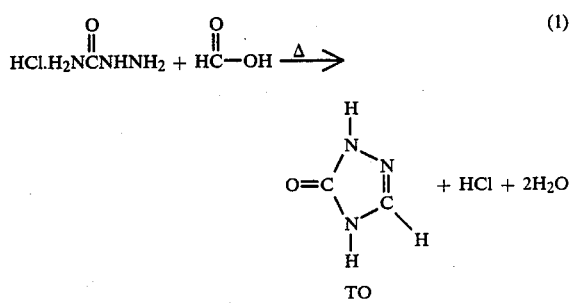

II. Preparation of NTO:

About 500 ml of 70% nitric acid was then gradually added to the cooled flask containing the TO mixture. The resulting mixture was heated to agitated boiling (55°–60° C.). The reaction is exothermic and brown fumes evolved. After the reaction was completed, the product was chilled to 5° C. in an ice bath, and the NTO solid collected by filtration. The collected product was further washed with ice water to remove excess nitric acid. Pure NTO was obtained by recrystallization from water followed by drying in an oven at 70° C. for approximately 24 hours. The purity of the NTO thus obtained was determined by both $^1$H NMR and $^{13}$C NMR spectroscopy. The presence of inorganic ions, if any, was determined by ion chromatography.

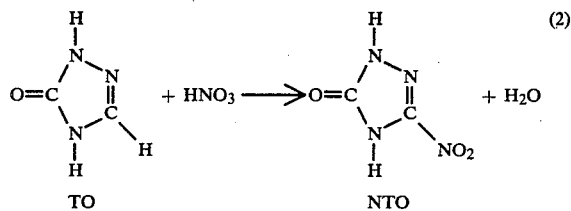

The chemical properties of NTO were determined and are presented in Table I. Physical and explosive properties of this material were determined and a comparison with those for RDX is presented in Table II hereof. NTO is a white crystalline compound, moderately soluble in water to give yellow solutions. It is relatively acidic (pKa=3.67), and forms stable salts with mono- or bivalent metals. The potassium, sodium, and lithium salts of NTO have been reported, as have those for ammonium and ethylenediaminium. The CO-balanced explosive was found to have a crystal density of about 1.93 g/cm$^3$ by x-ray crystallography. It can be seen from Table II that NTO is less sensitive and more stable than RDX in all of the texts. Additionally, the pyrolysis temperature for gas evolution from NTO was found to be greater than 260° C., while that for RDX is 160° C.

TABLE I
CHEMICAL PROPERTIES OF NTO

| | |
|---|---|
| Structural Formula: | 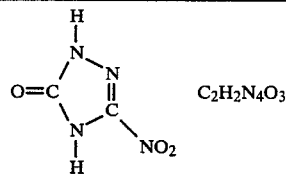 C$_2$H$_2$N$_4$O$_3$ |
| Molecular Weight: | 130 |
| Acidity: | pka = 3.67$^1$ |
| NMR Spectrum: | |
| $^1$H NMR (DMSO-d$_6$): | 12.7 ppm (\NH/) |
| $^{13}$C NMR (DMSO-d$_6$): | 148.0 ppm (\C—NO$_2$/), |
| | 154.4 ppm (\C=O/) |
| Elemental Analysis: | |
| Calc: | C, 18.46; H, 1.54; N, 43.08 |

TABLE I-continued
CHEMICAL PROPERTIES OF NTO

| | |
|---|---|
| Found: | C, 18.78; H, 1.92; N, 43.47 |

TABLE II
PHYSICAL AND EXPLOSIVE PROPERTIES

| | NTO | RDX |
|---|---|---|
| Crystal Density (g/cm$^3$) | 1.93 | 1.806 |
| DTA Exotherm (°C.) | >236 | 210 |
| Heat of Formation (kcal/mole) | −14.30 | +14.71 |
| Henkin Critical Temp (°C.) (0.64 mm size) | 237 | 219.6 |
| Impact Sensitivity (cm) | | |
| Type 12 | 291 | 22 |
| Type 12B | 293 | 41 |
| Spark Sensitivity (J) | | |
| 3 mil | 0.91 | 0.22 |
| 10 mil | 3.40 | 0.55 |
| Vacuum Stability | | |
| (ml/g/48 h at 100° C.) | 0.2 | |
| (ml/g/48 h at 120° C.) | 0.3 | 0.12–0.9 |

Additional performance properties were evaluated by conducting unconfined plate-dent tests at various charge diameters and pressed densities. NTO can easily be pressed to desired densities without the use of binders. Results are presented in Table III hereof with a comparison with similar data for RDX and TATB.

In summary, an explosive compound with desirable characteristics has been identified. Initial small-scale sensitivity tests of NTO indicate that this material is much less sensitive than RDX and TNT in all respects, but more sensitive than TATB. Results from a 4.13 cm diameter, unconfined plate-dent test for NTO at 92.2% of crystal density gave the detonation pressure predicted for NTO by the BKW calculation. This is equal to that measured for TATB at 96.5% of crystal density. However, other small scale tests at higher charge densities and/or smaller diameters gave less than the calculated performance indicating that NTO may have a large failure diameter. NTO is also derived from inexpensive starting materials.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

TABLE III
DETONATION PROPERTIES

| Explosive | Charge Density (g/cm$^3$) | Charge Diameter (cm) | P$_{CJ}$ (kbar) Measured | BKW |
|---|---|---|---|---|
| NTO | 1.93 (100% TMD) | — | — | 349 |
| | 1.781 (92.2% TMD) | 4.13 | 278 | 284 |
| | 1.782 (92.3% TMD) | 2.54 | 240 | 284 |
| | 1.855 (96.1% TMD) | 2.54 | Failed | 316 |
| | 1.759 (91.1% TMD) | 1.27 | 250 | 271 |
| RDX | 1.767 (97.8% TMD) | 4.12 | 338 | 348 |

TABLE III-continued

| Explosive | Charge Density (g/cm³) | Charge Diameter (cm) | $P_{CJ}$ (kbar) Measured | BKW |
|---|---|---|---|---|
| | DETONATION PROPERTIES | | | |
| TATB | 1.87 (96.5%) | 4.12 | 277 | 313 |

What we claim is:

1. A method for providing explosive chemical energy to an object, said method comprising the step of detonating the composition of matter which comprises 3-nitro-1,2,4-triazol-5-one.

2. A method for providing shock and impact insensitive explosive chemical energy to an object, said method comprising the step of detonating the composition of matter which comprises 3-nitro-1,2,4-triazol-5-one.

3. A method for providing explosive chemical energy to an object, said method comprising the step of detonating the composition of matter which consists essentially of 3-nitro-1,2,4-triazol-5-one.

4. A method for providing shock and impact insensitive explosive chemical energy to an object, said method comprising the step of detonating the composition of matter which consists essentially of 3-nitro-1,2,4-triazol-5-one.

5. A method for providing explosive chemical energy to an object, said method comprising the steps of pressing a composition of matter which consists essentially of 3-nitro-1,2,4-triazol-5-one into a chosen shape, and detonating the explosive formed thereby.

6. A method for providing shock and impact insensitive explosive chemical energy to an object, said method comprising the step of pressing a composition of matter which consists essentially of 3-nitro-1,2,4-triazol-5-one into a chosen shape, and detonating the explosive formed thereby.

* * * * *